US012446789B2

(12) United States Patent
Yoshifuji

(10) Patent No.: US 12,446,789 B2
(45) Date of Patent: Oct. 21, 2025

(54) BIOLOGICAL INFORMATION DETECTION APPARATUS AND BIOLOGICAL INFORMATION DETECTION SYSTEM

(71) Applicant: SONY GROUP CORPORATION, Tokyo (JP)

(72) Inventor: Kazunari Yoshifuji, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/700,412

(22) PCT Filed: Sep. 8, 2022

(86) PCT No.: PCT/JP2022/033737
§ 371 (c)(1),
(2) Date: Apr. 11, 2024

(87) PCT Pub. No.: WO2023/067936
PCT Pub. Date: Apr. 27, 2023

(65) Prior Publication Data

US 2024/0398248 A1 Dec. 5, 2024

(30) Foreign Application Priority Data

Oct. 20, 2021 (JP) ................................ 2021-171845

(51) Int. Cl.
*A61B 5/024* (2006.01)
*A61B 5/00* (2006.01)

(52) U.S. Cl.
CPC ........ *A61B 5/02427* (2013.01); *A61B 5/6817* (2013.01); *A61B 5/7405* (2013.01);
(Continued)

(58) Field of Classification Search
CPC . A61B 5/02427; A61B 5/6817; A61B 5/7405; A61B 5/742; H04R 25/656;
(Continued)

(56) References Cited

U.S. PATENT DOCUMENTS 6,283,915 B1 * 9/2001 Aceti .................. H04R 25/609 128/903
2011/0268308 A1 * 11/2011 Vasquez ............... H04R 1/1016 381/380

(Continued)

FOREIGN PATENT DOCUMENTS

JP 06-319705 A 11/1994
JP 2007-037750 A 2/2007

(Continued)

OTHER PUBLICATIONS

International Search Report and Written Opinion of PCT Application No. PCT/JP2022/033737, issued on Nov. 1, 2022, 10 pages of ISRWO.

*Primary Examiner* — John D Li
(74) *Attorney, Agent, or Firm* — CHIP LAW GROUP

(57) ABSTRACT

A biological information detection apparatus of the present disclosure includes a body and a wearing member. The body is provided with a first sensor that acquires first information regarding a living body. The wearing member is rotatably held by the body and is wearable in an ear hole of the living body. Rotation of the wearing member with respect to the body changes a posture of the body with respect to the wearing member.

10 Claims, 8 Drawing Sheets

(52) U.S. Cl.
CPC ........ *A61B 5/742* (2013.01); *A61B 2560/045* (2013.01); *A61B 2560/0462* (2013.01); *A61B 2562/0257* (2013.01)

(58) Field of Classification Search
CPC H04R 2460/11; H04R 1/1016; H04R 1/1041; H04R 5/033; H04R 1/105; H04R 2225/023; H04R 1/1008; H04R 25/604; H04R 25/652; H04R 1/1066; H04R 2225/021; H04R 2225/61; H04R 1/10; H04R 2460/13; H04R 25/606; H04R 5/0335; H04R 1/1075; H04R 2420/09; H04R 25/602; H04R 25/654; H04R 19/005; H04R 1/02; H04R 2460/05; H04R 2460/09; H04R 2460/15; H04R 25/40; H04R 25/402; H04R 25/45; H04R 25/48; H04R 25/60; H04R 25/608; H04R 25/65; H04R 25/658; H04R 5/02; H04R 5/027; A61N 1/0541; A61N 1/36036; A61N 1/375; A61F 11/08; A61F 2007/0005; A61F 2/18; G10K 2210/1081; G10K 11/002; G10K 11/004; G10K 11/162; G10K 11/17857; G10K 2210/3055; G10K 2210/3219; A61H 2205/027
See application file for complete search history.

(56) References Cited

U.S. PATENT DOCUMENTS

| | | | | |
|---|---|---|---|---|
| 2013/0066218 | A1 | 3/2013 | Kim | |
| 2013/0296731 | A1 * | 11/2013 | Kidmose | A61B 5/38 600/544 |
| 2016/0162256 | A1 * | 6/2016 | Komaromi | H04Q 9/00 340/870.07 |
| 2017/0195766 | A1 * | 7/2017 | Magariyachi | H04R 1/1016 |
| 2023/0380927 | A1 * | 11/2023 | Jeon | A61B 90/39 |

FOREIGN PATENT DOCUMENTS

| | | | |
|---|---|---|---|
| JP | 2008-168051 | A | 7/2008 |
| JP | 2018-027324 | A | 2/2018 |
| JP | 2020-116369 | A | 8/2020 |
| KR | 10-2017-0105740 | A | 9/2017 |

* cited by examiner

[ FIG. 1 ]
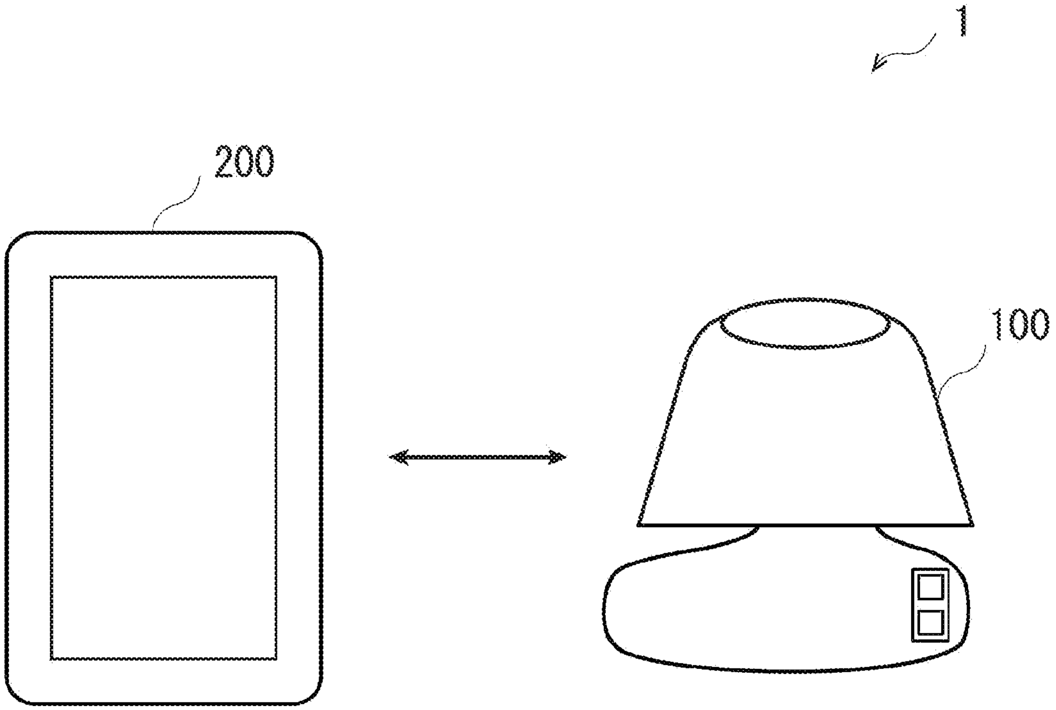

[ FIG. 2 ]
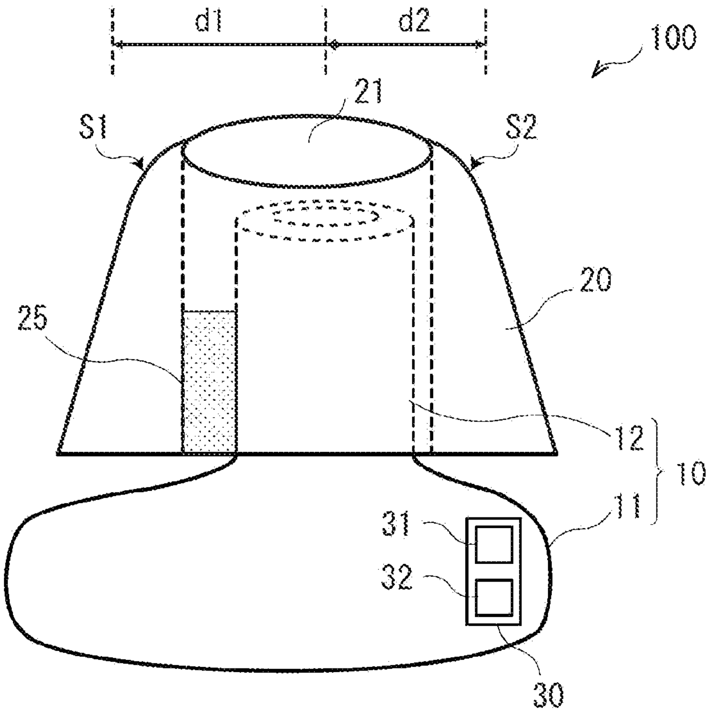
[ FIG. 3 ]
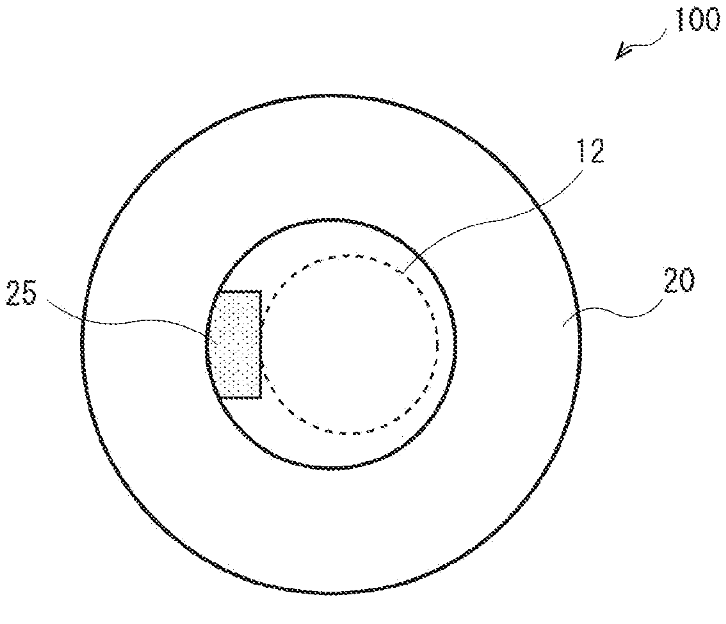

[ FIG. 4 ]
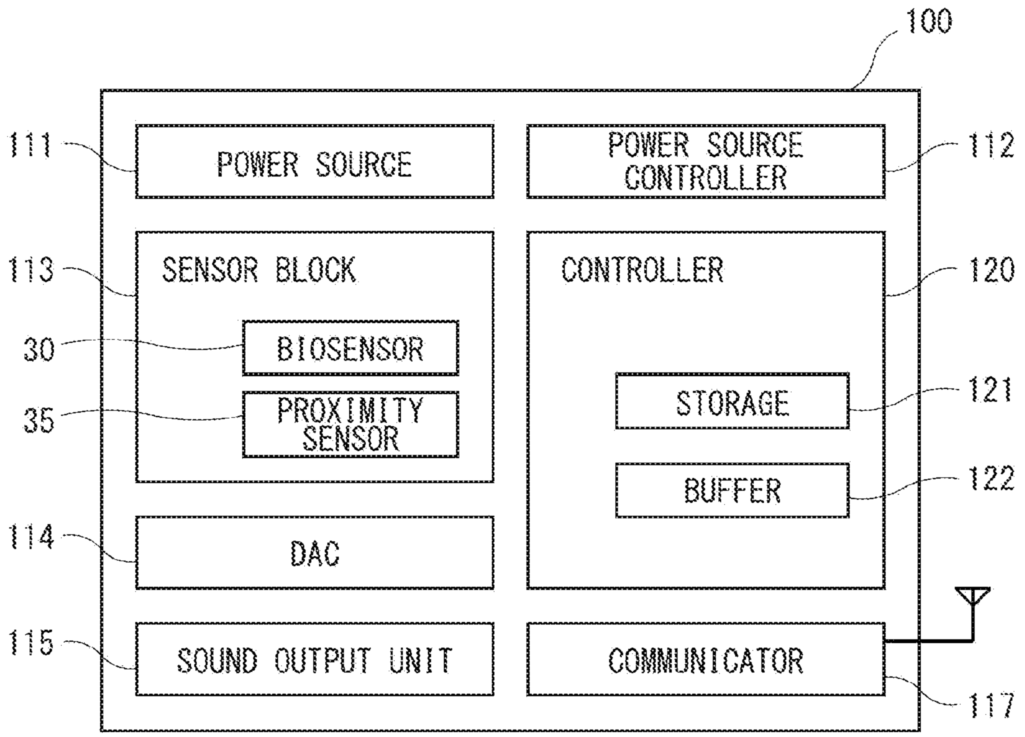

[ FIG. 5 ]
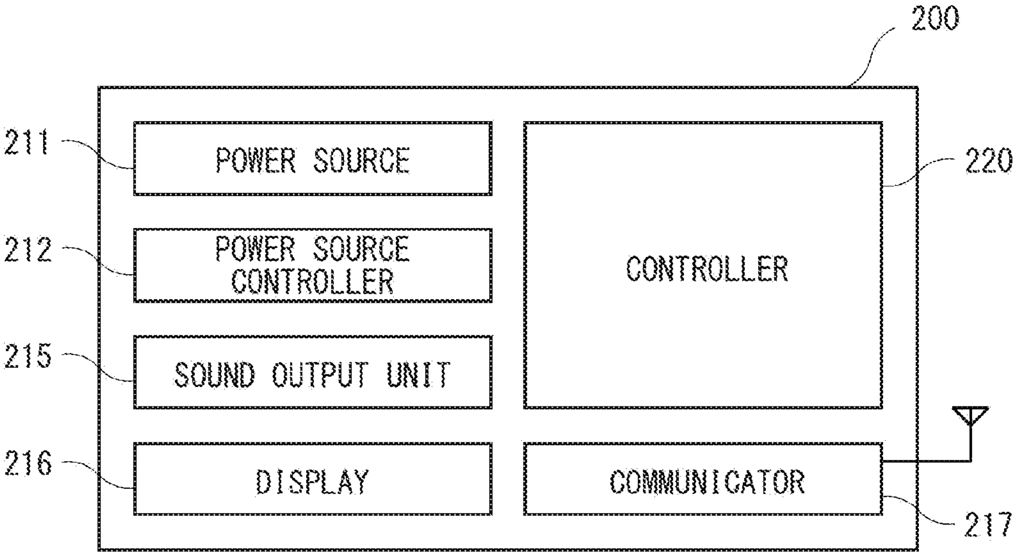

[ FIG. 6 ]
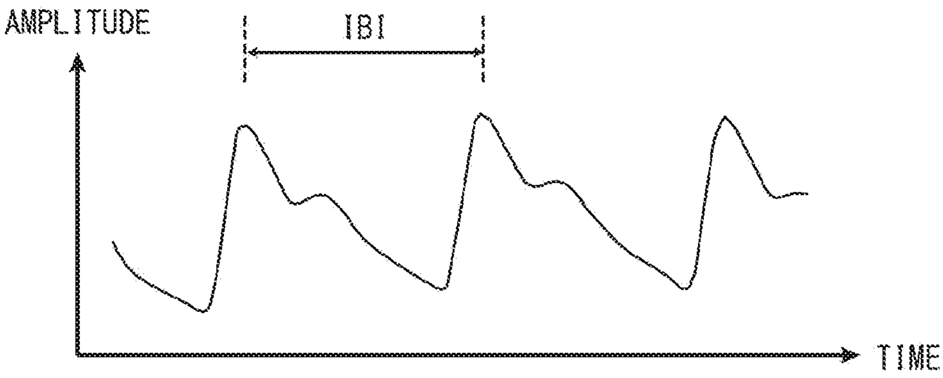

[ FIG. 7 ]
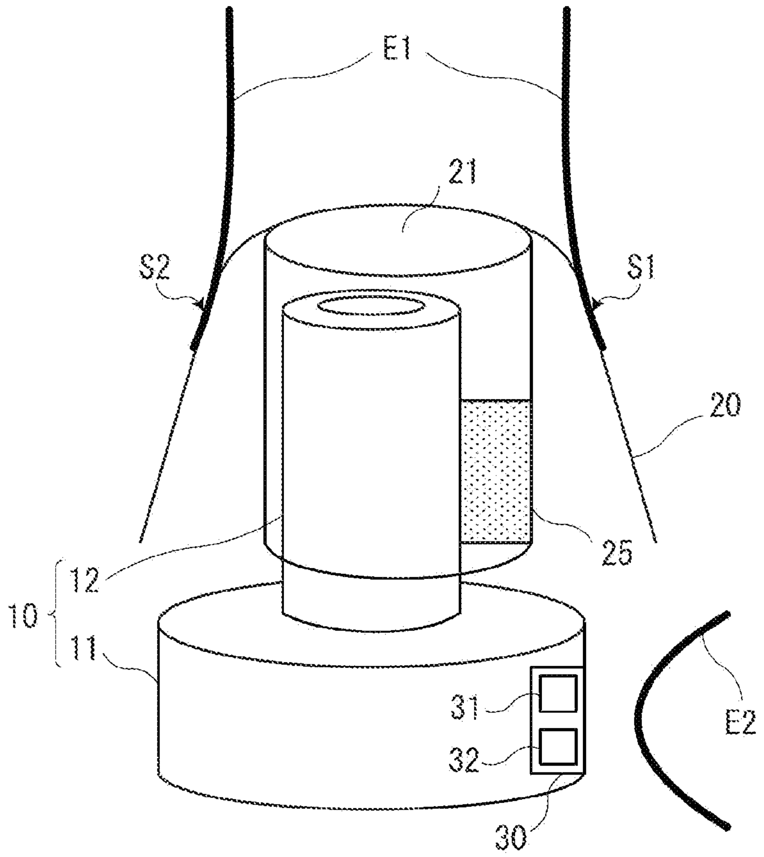

[ FIG. 8 ]
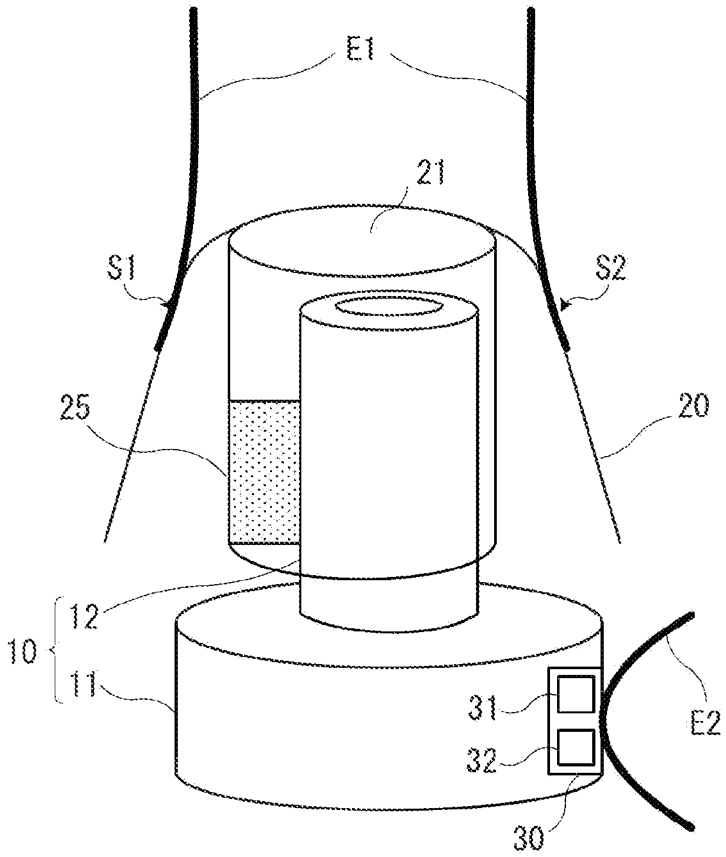

[ FIG. 9 ]
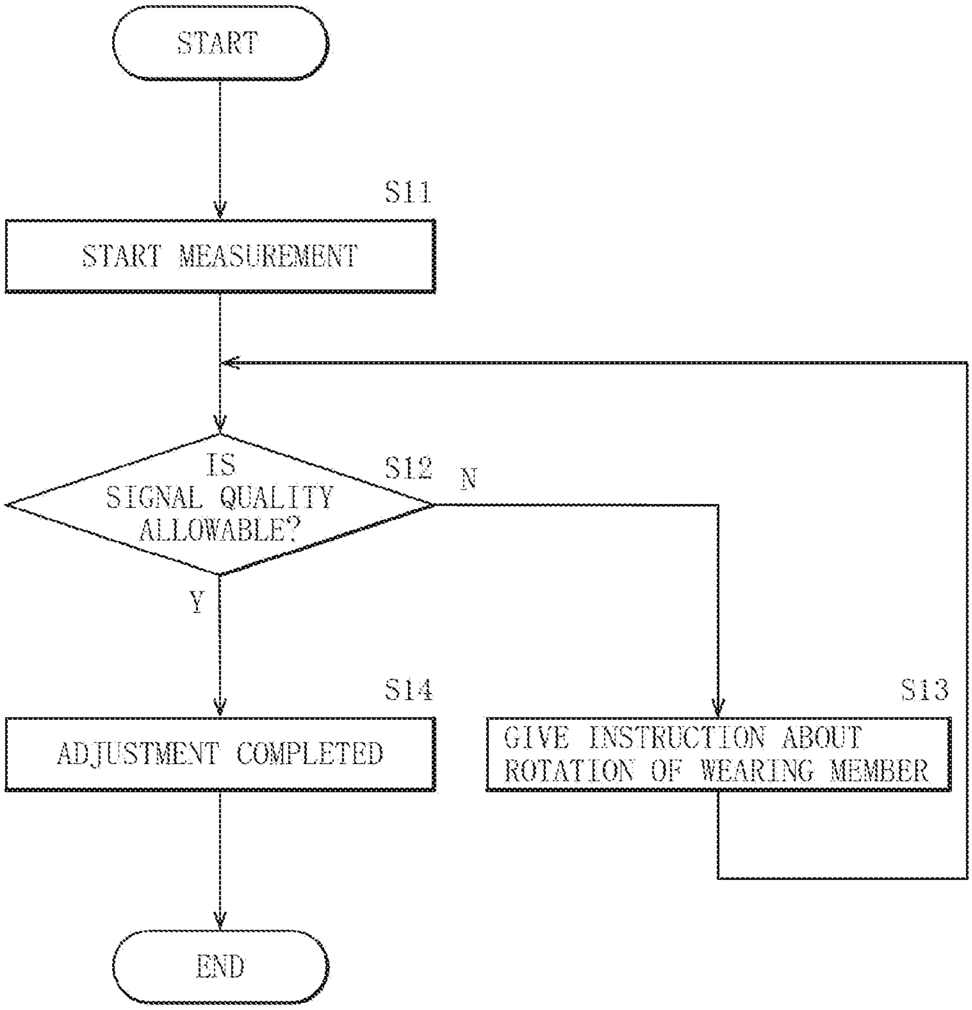

BIOLOGICAL INFORMATION DETECTION APPARATUS AND BIOLOGICAL INFORMATION DETECTION SYSTEM

CROSS REFERENCE TO RELATED APPLICATIONS

This application is a U.S. National Phase of International Patent Application No. PCT/JP2022/033737 filed on Sep. 8, 2022, which claims priority benefit of Japanese Patent Application No. JP 2021-171845 filed in the Japan Patent Office on Oct. 20, 2021. Each of the above-referenced applications is hereby incorporated herein by reference in its entirety.

TECHNICAL FIELD

The present disclosure relates to a biological information detection apparatus and a biological information detection system.

BACKGROUND ART

An apparatus has been proposed that includes an earpiece provided with a sensor electrode adapted to detect a potential of a living body, and measures a brain wave with use of the potential detected by the sensor electrode (PTL 1).

CITATION LIST

Patent Literature

PTL 1: Japanese Unexamined Patent Application Publication No. 2020-116369

SUMMARY OF THE INVENTION

Regarding an apparatus that detects biological information, it is desirable to improve a detection performance.

It is desirable to provide a biological information detection apparatus that makes it possible to achieve a higher detection performance.

A biological information detection apparatus according to one embodiment of the present disclosure includes a body and a wearing member. The body is provided with a first sensor configured to acquire first information regarding a living body. The wearing member is rotatably held by the body and is wearable in an ear hole of the living body. Rotation of the wearing member with respect to the body changes a posture of the body with respect to the wearing member.

A biological information detection system according to one embodiment of the present disclosure includes a biological information detection apparatus and an electronic apparatus. The biological information detection apparatus includes a body, a wearing member, and a transmitter. The body is provided with a first sensor configured to acquire first information regarding a living body. The wearing member is rotatably held by the body and is wearable in an ear hole of the living body. The transmitter transmits the first information. The electronic apparatus includes a receiver and a controller. The receiver receives the first information. The controller generates second information regarding a rotation amount of the wearing member with respect to the body on the basis of the first information. Rotation of the wearing member with respect to the body changes a posture of the body with respect to the wearing body.

BRIEF DESCRIPTION OF DRAWINGS

FIG. 1 is a diagram illustrating a configuration example of a biological information detection system according to an embodiment of the present disclosure.

FIG. 2 is a diagram illustrating a configuration example of a biological information detection apparatus according to the embodiment of the present disclosure.

FIG. 3 is a diagram illustrating an example of a cross-sectional configuration of the biological information detection apparatus according to the embodiment of the present disclosure.

FIG. 4 is a block diagram illustrating a configuration example of the biological information detection apparatus according to the embodiment of the present disclosure.

FIG. 5 is a block diagram illustrating a configuration example of an electronic apparatus according to the embodiment of the present disclosure.

FIG. 6 is a diagram illustrating an example of a waveform of a biological signal obtained by the biological information detection apparatus according to the embodiment of the present disclosure.

FIG. 7 is a diagram illustrating an example of a worn state of the biological information detection apparatus according to the embodiment of the present disclosure.

FIG. 8 is a diagram illustrating another example of the worn state of the biological information detection apparatus according to the embodiment of the present disclosure.

FIG. 9 is a flowchart illustrating an operation example of the biological information detection apparatus according to the embodiment of the present disclosure.

MODES FOR CARRYING OUT THE INVENTION

Some embodiments of the present disclosure will be described below in detail with reference to the drawings. Note that the description will be provided in the following order.

0. Background
1. Embodiment
2. Modifications
2-1. Modification 1
2-2. Modification 2
2-3. Modification 3
2-4. Modification 4
2-5. Modification 5

0. Background

In an apparatus in which a potential sensor or an optical sensor configured to acquire a signal (a biological signal) corresponding to a state of a living body is mounted, it is necessary to ensure a contact property between the sensor and the living body in order to acquire a biological signal with favorable signal quality. An apparatus of PTL 1 described above includes an assistance member adapted to stable attachment to a user's ear, and a mechanism configured to change an angle of a bearing portion of a canal-type earpiece to ensure a contact property of an electrode. However, because the mechanical mechanism is complicated, the size of the apparatus can increase and a manufacturing cost can increase. For this reason, it is desirable to use a simpler mechanism to ensure the contact property in relation to an ear that greatly varies in shape from individual to individual. In the following, a biological information detection system 1 according to an embodiment of the present disclosure will be described with reference to the drawings.

1. Embodiment

FIG. 1 is a diagram illustrating a configuration example of the biological information detection system 1 according to the embodiment of the present disclosure. The biological information detection system 1 includes a biological information detection apparatus 100 and an electronic apparatus 200. The biological information detection apparatus 100 is an electronic apparatus to be worn at an ear upon use. The electronic apparatus 200 is a terminal apparatus (a terminal) to be used by a user. The electronic apparatus 200 includes an electronic apparatus such as a smartphone, a tablet terminal, a wearable terminal, or a computer.

The biological information detection apparatus 100 is an earphone device, for example, a canal-type earphone. The biological information detection apparatus 100 is configured to be communicable with the electronic apparatus 200. In the biological information detection system 1, the biological information detection apparatus 100 is worn at an ear, and information regarding a living body (hereinafter referred to as biological information) is detected.

The biological information is, for example, information regarding a state of a human body as the living body. Examples of the biological information include information regarding a pulse wave, information regarding a brain wave, and information regarding a myoelectric potential. In the biological information detection system 1, the biological information such as the information regarding a pulse wave is acquired, which makes it possible to check a state of the living body.

FIG. 2 is a diagram illustrating a configuration example of the biological information detection apparatus 100 according to the embodiment. FIG. 3 is a diagram illustrating an example of a cross-sectional configuration of the biological information detection apparatus 100 according to the embodiment. FIG. 3 is a top view of the biological information detection apparatus 100 illustrated in FIG. 2. The biological information detection apparatus 100 will be described with reference to FIGS. 2 and 3.

The biological information detection apparatus 100 includes a body 10 and a wearing member 20. The body 10 includes a base 11 and a support 12. The wearing member 20 is a member wearable at an ear of a living body. The support 12 is a shaft portion extending from the base (base) 11. The wearing member 20 is detachably attached to the support 12. The wearing member 20 is attached to the support 12 of the body 10 and is rotatably held (supported) by the body 10.

The wearing member 20 includes, for example, an elastic material (rubber, resin, or the like). The wearing member 20 has a shape including a cylindrical shape having an opening 21 into which the support 12 is to be inserted. The wearing member 20 is supported by the support 12 as a result of insertion of the support 12 into the opening 21. The wearing member 20 is rotatably held with the support (a shaft portion) 12 serving as a rotational axis, and is rotatable relative to the body 10. Note that the wearing member 20 may include another flexible material or may include any other material.

The wearing member 20 has a shape corresponding to an ear hole of the living body, and is a member wearable in the ear hole. In an example illustrated in FIG. 2, the wearing member 20 has an umbrella-like (dome-like) shape. The wearing member 20 is an earpiece. The wearing member 20 attached to the body 10 is inserted into the ear hole upon actual use and is held by the ear of the user. When the wearing member 20 is inserted into the ear hole, a portion or all of the body 10 fits inside an auricle. Note that a plurality of wearing members 20 having different shapes and/or sizes may be prepared, and the wearing member 20 may be changed on the basis of the shape of the ear. The wearing member 20 may be referred to as a changeable earpiece.

The biological information detection system 1 may include a biological information detection apparatus 100 to be worn at a left ear and a biological information detection apparatus 100 to be worn at a right ear. The biological information detection apparatus 100 is applicable to a wireless earphone (or headphone) in which a right part and a left part are physically independent of each other. A sealed earpiece may be used as the wearing member 20. This makes it possible to reduce, when a user listens to a content such as music, an ambient environmental noise and allow the user to be more deeply immersed in the content.

The base 11 of the body 10 is provided with a sensor (hereinafter referred to as a biosensor) 30 configured to acquire biological information. The biosensor 30 is an optical sensor, a potential sensor, or the like, and acquires a signal (a biological signal) corresponding to the state of the living body. The biosensor 30 is, for example, a photoplethysmography (PPG: photoplethysmography) sensor, and acquires a biological signal regarding a pulse wave. In the biological information detection system 1, the biological signal is acquired by the biosensor 30, and a biological state is detected.

The biosensor 30 is, for example, a PPG sensor including a light emitter 31 and a light receiver 32, and measures the biological state. The light emitter 31 is a light-emitting device that includes a light source (for example, an LED (Light Emitting Diode)) and emits light. The light receiver 32 is a light reception device that includes a photodetector (Photodetector) and receives light. Wearing the wearing member 20 at the ear allows the biosensor 30 to come close to a portion of the ear (for example, near a tragus) that is a measurement site (a location to be measured).

Note that the measurement site is not limited to the tragus. The measurement site may be any site of the ear. The measurement site may be appropriately changed on the basis of the shape of the biological information detection apparatus 100 that is an earphone device, and may be a concha or any other portion.

The light emitter 31 irradiates the measurement site with light generated by the light source, in a state where the biosensor 30 and the measurement site are close to each other. The light emitted from the light emitter 31 is repeatedly absorbed and scattered in the body. While a portion of the light emitted from the light emitter 31 attenuates while repeatedly being absorbed and scattered, another portion thereof is received by the light receiver 32 side as optical feedback.

The light received by the light receiver 32 is light that has traveled through subcutaneous capillaries and has repeatedly absorbed in the body. Light having a wavelength within a range from 500 nm to 780 nm is often used as the light source of the light emitter 31, and light having a wavelength around 530 nm, in particular, is greatly absorbed by hemoglobin in blood. A blood volume in blood vessels increases and decreases in accordance with heart beats. As the blood volume increases and decreases, the amount of the absorbed light also increases and decreases. Therefore, the amount of light received by the light receiver 32 increases and decreases in accordance with the heart beats.

Performing photoelectric conversion in the light receiver 32 allows for acquisition of an electric signal corresponding to an increase or a decrease in the amount of the received light. As described above, the biosensor 30 irradiates the living body with light, receives the light that has traveled through subcutaneous capillaries and has repeatedly absorbed and scattered, and performs photoelectric conversion, to thereby acquire, as an electric signal, a biological signal based on a volume change of the blood in the blood vessels in the body.

For example, the biosensor 30 performs measurement on the tragus at a predetermined cycle, and repeatedly generates the biological signal. An amplitude (a signal level) of the biological signal changes (increases or decreases) in accordance with a change in the volume in the blood vessels accompanying the heart beats. Therefore, analyzing the biological signal generated by the biosensor 30 makes it possible to detect a pulse wave of the living body and calculate the biological information such as a heart rate.

FIG. 4 is a block diagram illustrating a configuration example of the biological information detection apparatus 100 according to the embodiment. The biological information detection apparatus 100 includes a power source 111, a power source controller 112, a sensor block 113, a DAC 114, a sound output unit 115, a communicator 117, and a controller 120. The power source 111, the power source controller 112, the sensor block 113, the DAC 114, the sound output unit 115, the communicator 117, and the controller 120 transmit and receive information by wired communication or wireless communication.

The power source 111 includes a battery (a storage battery), a converter, and the like, and is used to cause the biological information detection apparatus 100 to operate. The power source 111 includes, for example, a chargeable and large-capacity lithium-ion battery. The power source controller 112 includes a controller that controls the power source 111, and performs monitoring (management) of a battery capacity, a control of a charging operation, etc. The power source 111 is controlled by the power source controller 112, and supplies electric power to each unit of the biological information detection apparatus 100.

The sensor block 113 includes the biosensor 30 described above. In addition, the sensor block 113 includes, for example, a proximity sensor 35 that is a sensor that detects proximity of a user. The proximity sensor 35 is, for example, an infrared proximity sensor. The proximity sensor 35 applies infrared light to an outside, and detects approaching of an object to the proximity sensor 35 by reflected light of the applied light.

In addition, the sensor block 113 may include various sensors including, without limitation, a touch sensor serving as a user interface, a sensor that acquires a reference signal for noise cancellation of sound, an acceleration sensor, a gyro sensor (an angular velocity sensor), etc.

The DAC (Digital Analog Converter) 114 is a converter that converts a digital signal into an analog signal. The DAC 114 receives audio data (an audio signal), which is a digital signal, from the communicator 117 and the controller 120. The DAC 114 converts the received audio data into an analog signal.

The sound output unit 115 outputs a sound based on the audio data converted into the analog signal. The sound output unit 115 is a converter that includes a transducer (a driver) and converts the audio data, which is an electric signal, into a sound (a sound wave). The sound output unit 115 outputs a music (BGM), a sound effect, etc. on the basis of the audio data. The sound outputted from the sound output unit 115 propagates inside the support 12 illustrated in FIGS. 2 and 3, and is outputted to the outside from a tip of the wearing member 20.

The sound output unit 115 thus generates a sound on the basis of the received voice data. A sound from the sound output unit 115 travels inside the support 12 and is outputted to the ear hole in which the wearing member 20 is inserted. This allows the user to hear the music, etc. reproduced by the sound output unit 115.

The communicator 117 includes a communication module (for example, a Bluetooth (registered trademark) module) and is communicable with an external apparatus (the electronic apparatus 200 illustrated in FIG. 1 or the like). The communicator 117 is both a transmitter and a receiver, and transmits and receives information such as the biological information or the audio data. For example, the communicator 117 is configured to transmit the biological information acquired by the biological information detection apparatus 100 to the electronic apparatus 200. In addition, the communicator 117 receives the audio data by communication with the electronic apparatus 200.

The controller 120 includes a processor and a memory, and performs signal processing (information processing) on the basis of a program. The controller 120 includes a device such as a microprocessor, a CPU (central processing unit), or a DSP (Digital Signal Processor), and a memory such as a ROM or a RAM. The controller 120 reads and executes a program incorporated therein, and controls each unit of the biological information detection apparatus 100. The controller 120 is a signal processor that performs signal processing. The controller 120 performs communication including transmission and reception of information to and from the electronic apparatus 200 via the communicator 117.

In the example illustrated in FIG. 4, the controller 120 includes a storage 121 and a data buffer 122. The storage 121 includes a non-volatile memory. A program and data are to be stored (recorded) in the storage 121. The storage 121 contains various kinds of information including, without limitation, a program, a parameter, etc. to be used in a control of each unit of the biological information detection apparatus 100. The data buffer 122 is used, for example, in a case of exchanging a signal with another block, in a case of temporarily holding data at the time of calculation, etc.

The controller 120 supplies, to the biosensor 30, a signal adapted to control the biosensor 30, and controls an operation of the biosensor 30. The controller 120 causes the biosensor 30 to repeatedly perform measurement at a predetermined cycle and output the biological signal. The controller 120 performs signal processing on the biological signal received from the biosensor 30 to generate the biological information.

The controller 120 acquires audio data to be reproduced from the electronic apparatus 200 such as a smartphone via the communicator 117. The controller 120 performs signal processing on the audio data. Examples of the signal processing include a process of reducing a noise (a noise canceling process) and a process of correcting a signal amount. The audio data is subjected to signal processing by the controller 120 and thereafter converted into a digital signal by the DAC 114. The controller 120 causes the sound output unit 115 to output a sound corresponding to the audio data converted into the digital signal. In this way, the audio data is converted into a sound by the sound output unit 115, which allows the user to hear the sound.

FIG. 5 is a block diagram illustrating a configuration example of the electronic apparatus 200 according to the embodiment. The electronic apparatus 200 includes a power source 211, a power source controller 212, a sound output unit 215, a display 216, a communicator 217, and a controller 220. The power source 211, the power source controller 212, the sound output unit 215, the display 216, the communicator 217, and the controller 220 transmit and receive information by wired communication or wireless communication.

The power source 211 includes a battery and is used to cause the electronic apparatus 200 to operate. The power source controller 212 includes a controller that controls the power source 211, and performs monitoring of a battery capacity, etc. The power source 211 is controlled by the power source controller 212, and supplies electric power to each unit of the electronic apparatus 200. The sound output unit 215 is controlled by the controller 220, and outputs a sound on the basis of audio data. The display 216 is a liquid crystal display, an organic EL display, or the like, and displays an image on the basis of image data. The display 216 may include a touch panel.

The communicator 217 includes a communication module, and is communicable with an external apparatus (the biological information detection apparatus 100 illustrated in FIG. 1 or the like). The communicator 217 is both a transmitter and a receiver, and transmits and receives information such as the biological information or the audio data. For example, the communicator 217 communicates with the biological information detection apparatus 100 and receives the biological information. In addition, the communicator 217 transmits the audio data to the biological information detection apparatus 100.

The controller 220 includes a processor and a memory, and performs signal processing (information processing) on the basis of a program. The controller 220 includes a device such as a microprocessor, a CPU, or a DSP, and a memory such as a ROM or a RAM. The memory in the controller 220 contains various kinds of information including, without limitation, a program to be used in controlling each unit of the electronic apparatus 200, programs and data for various applications, etc.

The controller 220 reads and executes a program incorporated therein, and controls each unit of the electronic apparatus 200. The controller 220 is a signal processor that performs signal processing. The controller 220 transmits and receives information to and from the biological information detection apparatus 100 via the communicator 217.

For example, the user is able to perform various controls of the biological information detection apparatus 100, using an application on the electronic apparatus 200 as a user interface. To give an example, it is possible to control parameters related to music reproduction of the biological information detection apparatus 100, for example, equalization, etc.

FIG. 6 is a diagram illustrating an example of a waveform of the biological signal to be obtained by the biological information detection apparatus 100 according to the embodiment. In FIG. 6, a vertical axis represents an amplitude of the biological signal, and a horizontal axis represents time. The biological signal includes a DC component (a direct-current component) and an AC component (an alternating-current component). An amplitude of the biological signal varies in accordance with a volume variation in a blood vessel at the measurement site (e.g., the tragus).

An interval in a time-axis direction between adjacent peaks in a signal waveform is called an IBI (Inter-Beat-Interval). A heart rate, which represents the number of heart beats per minute, is representable by the following expression (1), using the peak-to-peak interval IBI (in seconds).

$$\text{Heart rate}=1/IBI[s]\times 60 \tag{1}$$

The controller 120 of the biological information detection apparatus 100 acquires a biological signal related to a pulse wave from the biosensor 30, calculates the time interval IBI, and calculates the heart rate using the foregoing expression (1). The controller 120 transmits information indicating the calculated heart rate as the biological information to the electronic apparatus 200 via the communicator 117.

The biosensor 30 performs measurement at predetermined time intervals, and sequentially outputs the generated biological signals to the controller 120. The controller 120 calculates the heart rate using the biological signals sequentially received from the biosensor 30, and generates biological information regarding the heart rate. The biological information generated by the biological information detection apparatus 100 is regularly or irregularly outputted to the electronic apparatus 200 via the communicator 117.

The controller 120 may output, to the electronic apparatus 200, the biological information including the biological signal and the information indicating the heart rate. The controller 220 of the electronic apparatus 200 may receive the biological signal from the biological information detection apparatus 100 as the biological information, and may calculate the time interval IBI, the heart rate, etc. on the basis of the received biological signal. Further, the method of determining the heart rate is not limited to the method of determining the heart rate using the above-described peak-to-peak interval IBL. A calculation expression other than the above-described expression (1) may be used.

Next, the biological information detection apparatus 100 will be further described with reference to FIGS. 2 and 3. The biological information detection apparatus 100 is configured to allow a posture of the body 10 to be changed with respect to the wearing member 20 by rotation of the wearing member 20 with respect to the body 10. This makes it possible to change a contact state between the biosensor 30 and the living body. The biological information detection apparatus 100 according to the present embodiment is configured to have a thickness that differs between one side and another side on a circumference of the opening 21. For example, the wearing member 20 has a thickness that differs between a portion on the circumference of the opening 21 at a portion in contact with the support 12 and another portion thereof. In the examples illustrated in FIGS. 2 and 3, a protrusion 25 is provided at a portion of an inner circumference of the opening 21. The protrusion 25 is a protruding member.

For example, the protrusion 25 is provided integrally with the wearing member 20, and protrudes from the inner circumference of the opening 21 toward the middle of the opening 21. The protrusion 25 is a protruding part extending from the inner circumference of the opening 21 toward the support 12. The protrusion 25 may also be regarded as a projecting portion projecting toward the support 12.

As illustrated in FIGS. 2 and 3, providing the protrusion 25 allows a center position of the opening 21 to be different from a center position of the support 12 in a direction intersecting a direction of insertion of the support 12 into the opening 21. In other words, the center position of the opening 21 is different from the center position of the support 12 on a plane orthogonal to the insertion direction of the support 12. Note that the shape of the protrusion 25 is not particularly limited, and may be a rectangular shape, a circular shape, or any other shape.

A first surface S1 and a second surface S2 of the wearing member 20 illustrated in FIG. 2 are surfaces configured to be in contact with a skin surface of the living body. Insertion of the wearing member 20 into the ear hole upon actual use may allow the first surface S1 and the second surface S2 to be in contact with the ear hole. The first surface S1 and the second surface S2 are positioned at respective distances (spacings) from the support 12 (the shaft) that are different from each other.

As illustrated in FIG. 2, the center of the first surface S1 is positioned at a distance d1 from the center of the support 12. In addition, the center of the second surface S2 is positioned at a distance d2 from the center of the support 12. Note that in the example illustrated in FIG. 2, d1>d2 holds.

FIG. 7 and FIG. 8 are each a diagram illustrating an example of a worn state of the biological information detection apparatus 100 according to the embodiment. FIG. 7 and FIG. 8 each illustrate an example case where the wearing member 20 is inserted into an ear hole E1, and the biosensor 30 is positioned near a tragus E2 that is the measurement site.

It is possible to change relative positions of the wearing member 20 and the biosensor 30 to a state illustrated in FIG. 7 or a state illustrated in FIG. 8, by relatively rotating the wearing member 20 with respect to the body 10 in which the biosensor 30 is mounted. Rotation of the wearing member 20 changes relative positions of a skin of the living body (the tragus E2 in FIGS. 7 and 8) and the biosensor 30.

FIG. 7 illustrates a case in which the wearing member 20 is attached to the support 12 to allow the protrusion 25 to be positioned on a right side of the support 12. In this case, the center position of the support 12 is shifted to a left side by an amount corresponding to the thickness of the protrusion 25 from the center position of the opening 21. The center position of the opening 21 is positioned on the right side relative to the center position of the support 12 in a direction orthogonal to the direction of the insertion of the support 12 into the opening 21.

In addition, in FIG. 7, the first surface S1 of the first surface S1 and the second surface S2 of the wearing member 20 is disposed at a position relatively close to the biosensor 30, and the second surface S2 is disposed at a position relatively far from the biosensor 30. The wearing member 20 is attached to the support 12 in a posture in which the first surface S1 is close to the biosensor 30. In this case, when the wearing member 20 is inserted into the ear hole E1 of the user as schematically illustrated in FIG. 7, the biosensor 30 and the tragus E2 can be separated away from each other depending on a size and a shape of the ear of the user.

FIG. 8 illustrates a case where the wearing member 20 is attached to the support 12 to allow the protrusion 25 to be positioned on the left side of the support 12. Rotating the wearing member 20 with respect to the body 10 changes the position of the protrusion 25, making it possible to change the state from that illustrated in FIG. 7 to that illustrated in FIG. 8. In the case of FIG. 8, the center position of the support 12 is shifted to the right side by an amount corresponding to the thickness of the protrusion 25 from the center position of the opening 21. The center position of the opening 21 is positioned on the left side relative to the center position of the support 12 in the direction orthogonal to the direction of the insertion of the support 12 into the opening 21.

In addition, in FIG. 8, the first surface S1 of the first surface S1 and the second surface S2 of the wearing member 20 is disposed at a position relatively far from the biosensor 30, and the second surface S2 is disposed at a position relatively close to the biosensor 30. The wearing member 20 is attached to the support 12 in a posture in which the second surface S2 is close to the biosensor 30. This allows the biosensor 30 to be closer to the tragus E2 than in the case of FIG. 7. As schematically illustrated in FIG. 8, when the wearing member 20 is inserted into the ear hole E1 of the user, the biosensor 30 and the tragus E2 come into contact with each other.

As described above, the rotation of the wearing member 20 with respect to the body 10 makes it possible to change the posture of the body 10 with respect to the wearing member 20. The rotation of the wearing member 20 with respect to the body 10 changes relative positions of a portion of the wearing member 20 that is to be in contact with the ear hole E1 and the biosensor 30, and changes a distance from the biosensor 30 to the tragus E2. Therefore, it is possible to adjust the contact property between the biosensor 30 and the tragus E2.

The controller 120 of the biological information detection apparatus 100 determines a reliability level (reliability) of the biological signal, i.e., signal quality of the biological signal. For example, the controller 120 determines the reliability level of the biological signal on the basis of the heart rate calculated using the biological signal. Typically, a person's heart rate is within a range from 40 beats/min to 200 beats/min. The controller 120 determines whether or not the calculated heart rate is within an allowable value (40 beats/min to 200 beats/min). In a case where the heart rate is within the allowable value, the controller 120 determines (judges) that the biological signal is acquired properly.

In contrast, when the heart rate exceeds the allowable value, the controller 120 determines that the biological signal is not acquired properly. In this case, the controller 120 may cause the sound output unit 115 to output an audio message indicating that the biological signal is not acquired properly, an audio message instructing (requesting) the rotation of the wearing member 20, etc.

The controller 120 calculates a rotation amount of the wearing member 20 necessary for contact between the biosensor 30 and the measurement site, using the biological signal. For example, the controller 120 compares the heart rate calculated using the biological signal with a predetermined reference value, to estimate the rotation amount (an angle) of the wearing member 20 necessary for bringing the biosensor 30 and the measurement site into contact with each other, and generate information regarding the rotation amount (the angle) of the wearing member 20. The controller 120 may cause the sound output unit 115 to output a sound indicating the necessary rotation amount of the wearing member 20 on the basis of the generated information regarding the rotation amount of the wearing member 20.

The controller 120 may transmit information indicating a result of the determination, information indicating the rotation amount of the wearing member 20, etc. to the electronic apparatus 200 via the communicator 117. The controller 220 of the electronic apparatus 200 may cause the display 216 of the electronic apparatus 200 to display an image indicating that the biological signal is not acquired properly, an image indicating the necessary rotation amount of the wearing member 20, etc. on the basis of the information transmitted from the biological information detection apparatus 100.

The controller 220 of the electronic apparatus 200 may cause the sound output unit 215 to output a sound indicating that the biological signal is not acquired properly, a sound indicating the rotation amount of the wearing member 20, etc. In addition, the controller 220 of the electronic apparatus 200 may cause the sound output unit 215 to output a sound prompting the user to replace the wearing member 20. It is possible for the user to appropriately adjust the contact property of the biosensor 30 by rotating the wearing member 20 while checking the guidance by the audio message outputted by the sound output unit 215, the image displayed on the display 216, etc. Note that the shape of the ear varies from individual to individual, which can make it difficult to calculate the rotation amount necessary for improving signal quality. Meanwhile, it is necessary to simplify a procedure to be performed by the user. For this reason, for example, the rotation amount may be fixed at 90 degrees, and the user may be notified of such a fixed rotation amount.

Note that the method of determining the reliability level of the biological signal is not limited to the above-described method. For example, the reliability level of the biological signal may be determined on the basis of a maximum value or a minimum value of the biological signal. Further, the controller 220 of the electronic apparatus 200 may perform the process of determining the reliability level of the biological signal using the biological signal acquired from the biological information detection apparatus 100. The biological information detection apparatus 100 may receive information indicating a result of the determination, information indicating the rotation amount of the wearing member 20, etc. from the electronic apparatus 200, and may output a sound indicating that the biological signal is not acquired properly, a sound indicating the necessary rotation amount of the wearing member 20, etc.

In a PPG sensor, an LED, a photodetector (PD), an internal electric circuitry, and the like are insulated and protected by a protective member to be prevented from coming into direct contact with the living body. The protective member includes, for example, a transparent resin having a high light transmittance. If there is a spacing (a gap) between the protective member and the living body, much of light from the LED is reflected by the surface of the living body, and much of light entering the PD becomes a component that does not pass through the living body. In this case, a desired biological signal may not be obtained. Therefore, in order to acquire a biological signal with favorable signal quality, it is necessary to ensure the contact property between the biosensor and the living body. In addition, the size and the shape of the ear vary from individual to individual, and an assumable case is that the device in which the biosensor is mounted fits to a user having an average ear shape, but does not fit to other users.

To address this, as described above, the biological information detection apparatus 100 according to the present embodiment is configured to allow the posture of the body 10 with respect to the wearing member 20 to be changed by the rotation of the wearing member 20 with respect to the body 10. This makes it possible to adjust the contact property between the biosensor 30 mounted in the body 10 and the measurement site.

In the present embodiment, it is possible to detect the biological signal in a state where the biosensor 30 is in favorable contact with the measurement site, and it is possible to suppress quality deterioration of the biological signal. For example, it is possible to prevent inappropriate detection of the biological signal due to insufficient contact between the measurement site and the biosensor 30, and to prevent an increase in noise component to be mixed in the biological signal.

In addition, it is possible to allow the biological information detection apparatus 100, which is an earphone device, to be fitted to a user having an average ear shape and also to other users. In addition, it is possible to allow, without using a complicated mechanical mechanism, the biological information detection apparatus 100 to be adapted to an ear shape that greatly varies from individual to individual and to ensure the contact property of the biosensor 30. Accordingly, it is possible to suppress an increase in the size of the biological information detection apparatus 100 and to suppress an increase in a manufacturing cost of the biological information detection apparatus 100.

FIG. 9 is a flowchart illustrating an operation example of the biological information detection apparatus 100 according to the embodiment. An operation example of the biological information detection apparatus 100 will be described with reference to the flowchart of FIG. 9. For example, processes illustrated in FIG. 9 are started on the basis of a program stored in the memory, when the biological information detection apparatus 100 is turned on in response to an operation on the touch sensor or the like.

In step S11, the controller 120 of the biological information detection apparatus 100 outputs a signal instructing measurement of the biological state to the biosensor 30. In accordance with an instruction (a command) from the controller 120, the biosensor 30 starts the measurement of the biological state and repeatedly generates a biological signal.

In step S12, the controller 120 determines the signal quality of the biological signal generated by the biosensor 30, i.e., the reliability level of the biological signal. The controller 120 checks whether or not the heart rate obtained by using the biological signal is within the allowable value. If the heart rate is a value outside a range of the allowable value, the controller 120 determines that the signal quality of the biological signal is low, and proceeds to step S13. If the heart rate is within the range of the allowable value, the controller 120 determines that the signal quality of the biological signal is high, and proceeds to step S14.

In step S13, the controller 120 gives the user an instruction regarding the rotation operation of the wearing member 20, the necessary rotation amount of the wearing member 20, etc. by the sound outputted from the sound output unit 115. The user rotates the wearing member 20 on the basis of the sound giving guidance about the rotation amount of the wearing member 20, and adjusts the contact property of the biosensor 30. Thereafter, the controller 120 returns to step S12, and performs the process of determining the signal quality of the biological signal again.

When the controller 120 makes an affirmative determination in step S12 and proceeds to step S14, the controller 120 determines that the adjustment of the contact property of the biosensor 30 is completed. In this case, the controller 120 ends the process illustrated in the flowchart of FIG. 9.

[Workings and Effects]

The biological information detection apparatus 100 according to the present embodiment includes the body 10 and the wearing member 20. The body 10 is provided with the biosensor 30 configured to acquire the biological information. The wearing member 20 is rotatably held by the body 10 and is wearable in the ear hole E1 of the living body. Rotation of the wearing member 20 with respect to the body 10 changes the posture of the body 10 with respect to the wearing member 20.

As described above, in the biological information detection apparatus 100 according to the present embodiment, the rotation of the wearing member 20 with respect to the body 10 changes the posture of the body 10 with respect to the wearing member 20. This makes it possible to easily adjust the contact property between the biosensor 30 mounted in the body 10 and the living body, and to bring the biosensor 30 into favorable contact with the living body. It is therefore possible to acquire a high-quality biological signal and improve accuracy of detection of the biological information.

In the biological information detection apparatus 100 according to the present embodiment, it is possible to allow, without using a complicated mechanical mechanism, the biological information detection apparatus 100 to be adapted to an ear shape that greatly varies from individual to individual and to ensure the contact property of the biosensor 30. Because it is thus not necessary to provide a complicated mechanism in the biological information detection apparatus 100, it is possible to suppress an increase in manufacturing cost of the biological information detection apparatus 100.

Next, modifications of the present disclosure will be described. In the following, components similar to those in the above-described embodiment are denoted by the same reference numerals, and descriptions thereof will be omitted where appropriate.

2. Modifications

2-1. Modification 1

In the flowchart illustrated in FIG. 9, the biological information detection apparatus 100 starts the measurement of the biological state in step S11. In this case, the biological information detection apparatus 100 may start the measurement of the biological state in a case where proximity of the user is detected by the proximity sensor 35. The controller 120 is configured to cause the biosensor 30 to measure the biological state and output a biological signal in a case where it is detected that the biological information detection apparatus 100 is worn at the ear of the user.

2-2. Modification 2

The biosensor 30 may be a sensor configured to measure bioelectricity. For example, the biosensor 30 includes a plurality of electrodes adapted to detect a potential, for example, two electrodes, i.e., a first electrode and a second electrode. The first electrode and the second electrode are spaced apart from each other and are to be in contact with the measurement site at respective positions different from each other. The biosensor 30 detects the potential (a voltage) of the surface of the living body by the first electrode and the second electrode.

When the wearing member 20 is inserted into the ear hole upon actual use, the first electrode and the second electrode of the biosensor 30 come into contact with the measurement site (e.g., the tragus). Due to the electricity generated in the living body, a potential difference is generated between the first electrode and the second electrode of the biosensor 30 in contact with the skin of the living body. Note that one electrode of the first electrode and the second electrode or another electrode different from the first electrode and the second electrode may be used as a reference potential electrode.

For example, the biosensor 30 generates a biological signal having a voltage based on a difference between a potential of the first electrode and a potential of the second electrode. Note that the biosensor 30 may generate each of a biological signal based on the potential of the first electrode and a biological signal based on the potential of the second electrode.

The controller 120 of the biological information detection apparatus 100 determines the signal quality of the biological signal generated by the biosensor 30. The controller 120 determines the signal quality of the biological signal, for example, on the basis of an average value, a maximum value, a minimum value, a change amount, or the like of the voltages of the biological signals. In a case where the signal quality of the biological signal is determined as being low, the controller 120 controls, for example, the sound output unit to output a sound that gives guidance about the rotation of the wearing member 20.

The controller 120 is configured to detect the pulse wave of the living body and calculate the heart rate by analyzing the biological signal generated by the biosensor 30. Alternatively, the controller 120 may detect any other information regarding the living body, for example, a brain wave of the living body, by analyzing the biological signal.

In the case of the present modification also, it is possible to adjust the contact property of the biosensor 30 by rotating the wearing member 20. This makes it possible to detect the biological signal in a state in which the biosensor 30 is brought into sufficiently close contact with the measurement site. Accordingly, it is possible to suppress a decrease in accuracy of detection of the biological signal.

2-3. Modification 3

The biological information detection apparatus 100 may include a mechanism that allows the wearing member 20 to automatically rotate with respect to the body 10. In this case, the controller 120 of the biological information detection apparatus 100 may control a posture of the wearing member 20 on the basis of the rotation amount of the wearing member 20 determined on the basis of the biological signal, and may adjust the contact property of the biosensor 30 mounted in the body 10.

2-4. Modification 4

The biological information detection apparatus 100 may include a brain wave sensor configured to generate a biological signal regarding a brain wave. Alternatively, the biological information detection apparatus 100 may include a sensor such as a myoelectric sensor or a body temperature sensor. The biosensor 30 may be a brain wave sensor, a myoelectric sensor, or the like.

2-5. Modification 5

The technology according to the present disclosure is applicable to various products. For example, the technology according to the present disclosure may be applied to an inner-ear-type earphone, an ear-hook-type earphone, a hearing aid, etc.

Although the present disclosure has been described above with reference to the embodiment and the modifications, the present technology is not limited to the above-described embodiments and the like, and various modifications may be made. For example, the above-described modifications have been described as modifications of the above-described embodiment; however, it is possible to appropriately combine the respective configurations of the modifications with each other. In addition, although a human body is exemplified as the living body, it may be possible to apply the present disclosure to a living body other than the human body, for example, an animal such as a pet or a domestic animal.

Note that the effects described in the present description are mere examples and the description thereof is non-limiting. Other effects may also be achieved. Further, the present disclosure may have the following configurations.

(1)

A biological information detection apparatus including:

a body provided with a first sensor configured to acquire first information regarding a living body; and a wearing member that is rotatably held by the body and is wearable in an ear hole of the living body, in which rotation of the wearing member with respect to the body changes a posture of the body with respect to the wearing member.

(2)

The biological information detection apparatus according to (1) described above, in which the first sensor acquires the first information from the living body, and respective relative positions of the living body and the first sensor are to be changed by the rotation of the wearing member with respect to the body.

(3)

The biological information detection apparatus according to (1) or (2) described above, in which the wearing member is rotatable about an axis, and the wearing member includes a first surface and a second surface, the first surface being contactable with the ear hole and positioned at a first distance from the axis, the second surface being contactable with the ear hole and positioned at a second distance from the axis.

(4)

The biological information detection apparatus according to any one of (1) to (3) described above, in which the first sensor acquires the first information while being in contact with a skin of the living body.

(5)

The biological information detection apparatus according to any one of (1) to (4) described above, in which the body includes a support that supports the wearing member, and the wearing member has a cylindrical shape having an opening into which the support is to be inserted.

(6)

The biological information detection apparatus according to any one of (1) to (5) described above, in which a center position of the opening is different from a center position of the support in a direction intersecting with an insertion direction of the support.

(7)

The biological information detection apparatus according to any one of (1) to (6) described above, in which the wearing member has a thickness that differs between a portion on a circumference of the opening in a portion in contact with the support, and another portion on the circumference of the opening in the portion in contact with the support.

(8)

The biological information detection apparatus according to any one of (1) to (7) described above, in which the wearing member includes a protrusion on one side or another side of an inner circumference of the opening.

(9)

The biological information detection apparatus according to any one of (1) to (8) described above, in which the body includes a controller that generates second information regarding a rotation amount of the wearing member with respect to the body, on the basis of the first information acquired by the first sensor.

(10)

The biological information detection apparatus according to any one of (1) to (9) described above, in which the body includes a second sensor that detects proximity of a user, and the first sensor acquires the first information in a case where the proximity of the user is detected by the second sensor.

(11)

A biological information detection system including:

a biological information detection apparatus including a body, a wearing member, and a transmitter, the body being provided with a first sensor configured to acquire first information regarding a living body, the wearing member being rotatably held by the body and being wearable in an ear hole of the living body, the transmitter transmitting the first information; and an electronic apparatus including a receiver and a controller, the receiver receiving the first information, the controller generating second information regarding a rotation amount of the wearing member with respect to the body on the basis of the first information, in which rotation of the wearing member with respect to the body changes a posture of the body with respect to the wearing body.

The present application claims the benefit of Japanese Priority Patent Application JP2021-171845 filed with the Japan Patent Office on Oct. 20, 2021, the entire contents of which are incorporated herein by reference.

It should be understood by those skilled in the art that various modifications, combinations, sub-combinations and alterations may occur depending on design requirements and other factors insofar as they are within the scope of the appended claims or the equivalents thereof.

The invention claimed is:

1. A biological information detection apparatus, comprising:

a body that comprises:

a first sensor configured to acquire first information regarding a living body;

a base; and a support that is a shaft portion and that extends from the base; and a wearing member that is rotatably held by the body, wherein the wearing member is wearable in an ear hole of the living body, rotation of the wearing member with respect to the body changes a posture of the body with respect to the wearing member, the support is in an opening of the wearing member, the wearing member includes a protrusion on one of a first side or a second side of an inner circumference of the opening of the wearing member, and the protrusion extends from the inner circumference of the opening toward the support.

2. The biological information detection apparatus according to claim 1, wherein the first sensor is further configured to acquire the first information from the living body, and respective relative positions of the living body and the first sensor change based on the rotation of the wearing member with respect to the body.

3. The biological information detection apparatus according to claim 1, wherein the wearing member is rotatable about an axis, and the wearing member includes a first surface and a second surface, wherein the first surface is contactable with the ear hole, the first surface is at a first distance from the axis, the second surface is contactable with the ear hole, and the second surface is at a second distance from the axis.

4. The biological information detection apparatus according to claim 1, wherein the first sensor is further configured to acquire the first information, based on the first sensor being in contact with a skin of the living body.

5. The biological information detection apparatus according to claim 1, wherein the support is configured to support the wearing member, and the wearing member has a cylindrical shape having the opening.

6. The biological information detection apparatus according to claim 5, wherein a center position of the opening is different from a center position of the support, in a direction that intersects with an insertion direction of the support.

7. The biological information detection apparatus according to claim 5, wherein the wearing member has a thickness that differs between a first portion, on the inner circumference of the opening, in contact with the support, and a second portion on the inner circumference of the opening, in contact with the support.

8. The biological information detection apparatus according to claim 1, wherein the body further comprises a controller configured to generate second information regarding a rotation amount of the wearing member with respect to the body, based on the first information acquired by the first sensor.

9. The biological information detection apparatus according to claim 8, wherein the body further comprises a second sensor that detects configured to detect a proximity of a user, and the first sensor is further configured to acquire the first information in a case where the proximity of the user is detected by the second sensor.

10. A biological information detection system, comprising:

a biological information detection apparatus including a body, a wearing member, and a transmitter, wherein the body with comprises:

a first sensor configured to acquire first information regarding a living body;

a base; and a support that is a shaft portion and that extends from the base, the wearing member is rotatably held by the body, the wearing member is wearable in an ear hole of the living body, the transmitter is configured to transmit the first information; and an electronic apparatus including a receiver and a controller, wherein the receiver is configured to receive the first information, the controller is configured to generate second information, regarding a rotation amount of the wearing member with respect to the body, based on the first information, rotation of the wearing member with respect to the body changes a posture of the body with respect to the wearing member, the support is in an opening of the wearing member, the wearing member includes a protrusion on one of a first side or a second side of an inner circumference of the opening of the wearing member, and the protrusion extends from the inner circumference of the opening toward the support.

* * * * *